United States Patent [19]

Rieppel et al.

[11] 4,103,359
[45] Aug. 1, 1978

[54] NOISE SUPPRESSING WELDING HELMET

[75] Inventors: Perry J. Rieppel, Worthington; Harold Richard Henderson, Lancaster, both of Ohio

[73] Assignee: Arcair Company, Lancaster, Ohio

[21] Appl. No.: 773,633

[22] Filed: Feb. 28, 1977

[51] Int. Cl.² .............................................. A61F 9/06
[52] U.S. Cl. ............................................... 2/8; 2/209; 2/423
[58] Field of Search ........................ 2/8, 10, 209, 423; 179/156 R, 182 R; 181/33 A, 33 R

[56] References Cited

U.S. PATENT DOCUMENTS

| | | | |
|---|---|---|---|
| 2,016,775 | 10/1935 | Gingg | 2/8 |
| 2,889,555 | 6/1959 | Stuart et al. | 2/6 |
| 3,327,318 | 6/1967 | Stickney | 2/8 |
| 3,423,759 | 1/1969 | Catroppa et al. | 2/6 |
| 3,621,488 | 11/1971 | Gales | 2/209 X |
| 3,795,014 | 3/1974 | Simpson et al. | 179/182 X |

Primary Examiner—Peter Nerbun
Attorney, Agent, or Firm—James C. Simmons; Barry Moyerman; E. Eugene Innis

[57] ABSTRACT

A welder's helmet having means to reduce the level of noise reaching a welder's ears when the helmet is positioned for welding. The helmet is characterized by the fact that the sound reducing means while fixed to the helmet does not contact or rest upon the head, ears or face of the welder thus not interfering with normal atmosphere circulation between the welder's head and helmet.

11 Claims, 8 Drawing Figures

NOISE SUPPRESSING WELDING HELMET

BACKGROUND OF THE INVENTION

1. Field of the Invention

The present invention pertains to welding helmets for protecting the face and sides of a welder's head from being struck by molten metal, sparks, ultra violet and other radiation and other debris generated when a welding operation is taking place. Normally, the helmet features a front piece with a light filtering window so that the welder can watch the welding process while at the same time his eyes are protected from the intense light, including ultra violet and infra red radiaion, generated especially in an arc-welding operation. The front piece is generally a continuation of two rearwardly extending sides which serve to partially encircle the welder's head to protect the sides of the head from flying debris.

2. Description of the Prior Art

Except for the flexible ear portion covers, U.S. Pat. No. 3,327,318 discloses a conventional welder's helmet or mask as they are sometimes called. The conventional helmet includes a head piece or cradle which fits over the welder's head and supports the helmet (mask) in relation to the welder's head. Normally, the helmet is held in a spaced relationship to the welder's head so that air can circulate between the helmet and the welder's head to prevent excessive perspiration and discomfort due to heat.

Since there are adverse physiological conditions associated with most welding operations, considerable effort has been devoted to improving the welder's environment. The two major adverse physiological conditions are excessive noise and air pollution. In regard to the latter condition, U.S. Pat. Nos. 2,354,502 and 3,535,707 demonstrate attempts to modify existing welding helmets to provide means to control air pollution or otherwise upgrade the atmospheric conditions surrounding the welder's head.

As noted above, one attempt at reducing noise pollution or the adverse effects of noise is demonstrated by U.S. Pat. No. 3,327,318, which discloses means for accommodating sound attenuating ear muffs worn by the welder at the same time a welding helmet is worn in position for welding. Conventionally, noise abatement has followed the path of using ear muffs or sound attenuating ear cups which firmly engage the sides of the head while covering the ears.

In addition to the aforementioned patent, this method of noise abatement is disclosed in U.S. Pat. No. 3,621,488 in regard to a crash helmet. The major efforts in this type of sound attenuation have occurred in regard to crash hemlets, and in particular, to crash helmets or helmets worn by military air craft personnel. Examples of such devices are shown in U.S. Pat. Nos. 2,619,639; 2,802,214; 2,867,813; and 3,005,203.

It is well-known that the sound attenuating ear muffs are effective and are used widely in industry. However, the largest drawback of the sound attenuating ear muff is that it firmly grips the head of the wearer. Over long periods of time, e.g. an eight hour work shift, these ear muffs can create severe wearer discomfort from the physical pressure and from closing off air circulation thus promoting perspiration in and around the ears of the wearer.

SUMMARY OF THE INVENTION

In order to avoid some of the problems inherent in prior art safety helmets and welder's helmets that relied upon the use of ear muff-type sound attenuating devices, it has been discovered that a significant reduction in the noise level presented to a welder's ear can be achieved by positioning sound absorbing devices on a welding helmet in spaced relation to the welder's ear as set out in the following description.

According to the present invention, a welder's helmet is provided with a forward extending recess in each of the sides of the helmet which recesses are sized to be larger than the area normally covering the ears of a welder. Ear protection means, including an acoustical absorbing medium, is fitted into these recesses and extends rearwardly beyond the sides of the helmet so that the acoustical absorbing material is spaced apart from, but adjacent to, the ears of the welder/user. In addition, increased sound attenuation can be achieved by lining the entire inside surface of the helmet with sound absorbing material.

As another feature of the invention, existing welding helmets can be fitted with a device containing sound attenuating material which will provide effective noise reduction comparable to that of the newly developed welding helmet.

Therefore, it is the primary object of this invention to provide an improved welding helmet.

It is further object of this invention to provide an improved welding helmet with means for attenuating ambient noise presented to the welder/user's ear.

It is still a further object of the present invention to provide means for reducing noise pollution in a conventional welding helmet.

DETAILED DESCRIPTION OF THE PREFERRED EMBODIMENT

Figure 1:
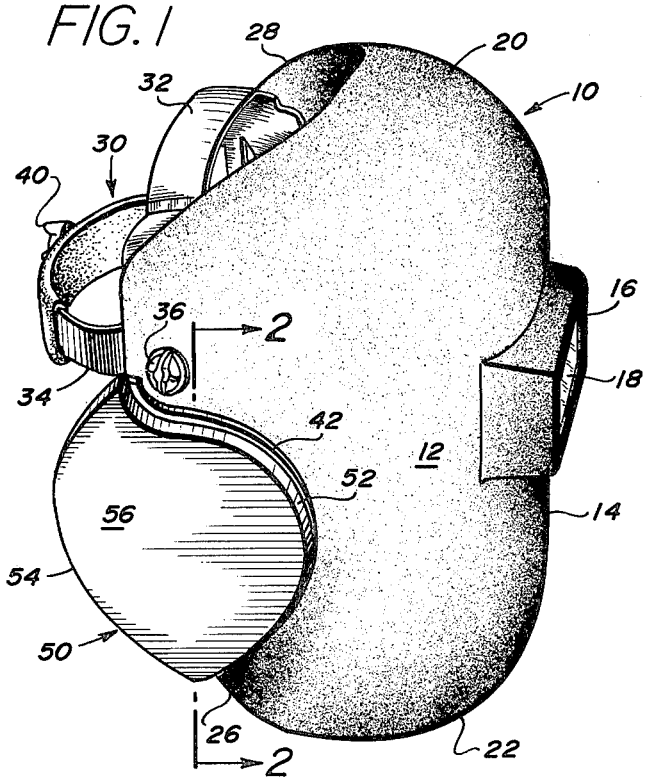
FIG. 1 is a perspective view of the helmet according to the present invention.

FIG. 1 shows a welding helmet designated generally as 10, which includes a face piece 12 formed of a hard and durable fire retardant synthetic material such as plastic, fiberglass or fiber reinforced synthetic sheet material. Face piece 12 is generally molded by pressing from sheet stock or is otherwise formed as a unitary structure having a generally cylindrical front section 14 having a window port or holder 16 including a shatter resistant light filtering glass 18. Front section 14 protects the face of the welder and provides means, through glass 18, whereby the welder can view the weld in progress without damage to the eyes. Window holder 16 can include means (not shown) for moving the light filtering window 18 out of position thus revealing a clear safety glass (not shown) so that eye protection is afforded to the welder when not welding. Face piece 12 includes a crown section 20 to protect the top forward portion of the welder's head and a depending skirt portion 22 to protect the chin and neck of the welder. Lastly, the face piece 12 includes rearwardly extending sides 26 and 28 for protecting each ear and the side of the head of the welder/user.

Face piece 12 is supported by head harness 30 which includes a top of the head strap 32 and adjustable encircling strap 34. The face piece 12 is caused to pivot in relation to the head strap 30 by means of adjustable pivot members 36 and 38. Thus, face piece 12 can be positioned in front of a welder's face (FIG. 3) for welding or moved away from the face thus allowing the welder an unobstructed view when the welding operation has been halted or terminated.

Head encircling member 34 includes a ratchet-type adjustment; and a snap-type adjustment (not shown) is included in strap 32 so that harness 30 can be adjusted for different head sizes. Adjustment of member 34 is accomplished by means of adjusting knob 40.

Figure 2:
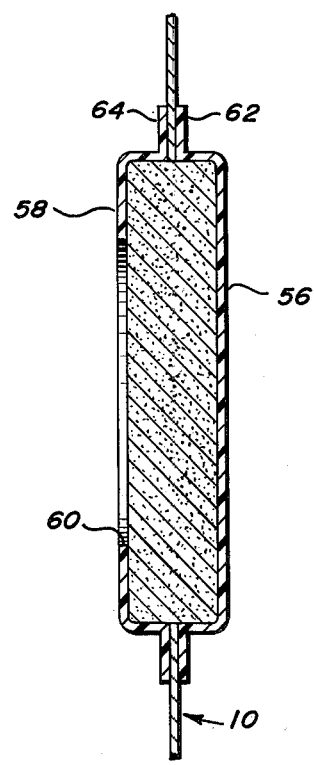
FIG. 2 is a fragmentary section taken along the lines 2—2 of FIG. 1.
Figure 3:
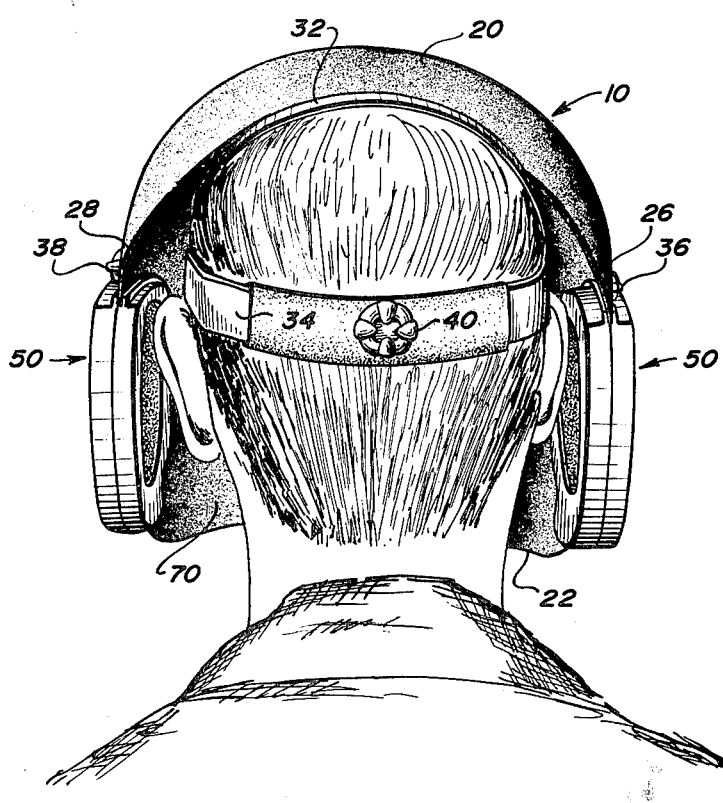
FIG. 3 is a rear view showing the helmet on the head of a welder/user in position for welding.

Formed in each side 26, 28 of face piece 12 of helmet 10 is a forward extending recess such as 42 shown in relation to side 26 of face piece 12. Disposed within recess 42 is an ear protector 50 which has a peripheral shape in its forward portion 52 complementary to the recess 42 in face piece 12. Ear protector 50 extends rearwardly of the face piece 12 as shown by the numeral 54 of FIG. 1. Ear protector 50 includes a rigid outer shell 50 and a complementary inner shell 58 having therein a large annular opening 60 (FIGS. 2 and 3). Disposed within ear protector 50 is a noise attenuating material such as a noise absorption foam manufactured and sold by the Composites Division of the Ferro Corporation of Norwalk, Connecticut under the trademark CUSTIFOAM, 3-D. Ear protector 50 includes complementary spaced apart lips 62, 64 which trace the periphery of the sides 56, 58 so that the ear protector 50 can be affixed to the face piece 12 as by a conventional cementing technique. Alternatively, rivets or other mechanical fasteners could be passed through the lips 62, 64 and the wall of face piece 12 to provide an intimate mechanical bond.

As shown in FIG. 3, when the helmet according to the present invention is donned by a welder/user and the helmet 10 is in position for the welder to commence a welding operation, the ear pieces 50 are positioned adjacent each ear of the welder, but do not touch the ear of the welder. Provision is made in the construction of the helmet to adjust the width of the "ear area." This can be done by an adjustable band in the chin area (skirt portion 22) of face piece 12 or around the back of the welder's head by an additional adjusting strap (not shown). With the sound absorbtion material as close to the user's ear as possible, without actually touching the ear, maximum sound reduction at the ear is achieved. Thus, the noise absorption material is positioned to attenuate the noise that is presented to a welder's ear area without pressing against the ear of the welder thus causing discomfort due to pressure on the ear or excessive perspiration by preventing air from freely circulating around the ears of the welder.

In particular, the welding helmet of FIGS. 1–3 is ideally suited for use with the conventional air-carbon arc cutting and gouging process developed by the Arcair Company of Lancaster, Ohio. In the air-carbon arc cutting and gouging process, metal cutting or grooving (preparation for subsequent welding) is achieved by using a torch which holds a carbon graphite electrode so that the welder can strike an arc between the electrode and the work piece to cause melting of the metal. At the same time, a stream of compressed air is directed along the electrode to "blow away" or remove the molten metal thus providing a cut or groove in the metal work piece. The air-carbon arc cutting and gouging process is inherently noisy, the noise generated by the process coming essentially from a point source which the operator faces. The helmet of the present invention was devised in an attempt to reduce the level of noise present at the user's ear without resorting to the conventional "ear-muff" type of ear protector.

In the air-carbon arc cutting and gouging process, reducing the noise level, measured 20 inches from the source of procedures approved by the American Welding Society, present at the welder's ear by a factor of 10 to 15 decibels would result in significantly improved operator comfort and lessen the tendency for permanent ear damage to operators using equipment employing the process.

Set forth in Table I is a summary of acoustical data measured at the arc in the air-carbon arc cutting and gouging process and at the welder's ear when the process is operating.

TABLE I

CARBON-GRAPHITE ELECTRODES AT HIGH AND LOW AIR FLOW

| Type of Torch | Type of Electrode | Air Flow (SCFH) | Power AMPS Volts | Noise Level, dba Outside Helmet | Users Ear |
|---|---|---|---|---|---|
| N-5 | ¼"* | 37 | 750–40 | 119.8–124.8 | 104.6–107.5 |
| N-5 | ¼"* | 24 | 750–40 | 113.3–115.6 | 102.0–104.0 |
| N-5 | ¼"** | 37 | 750–32 | 109.1–110.6 | 93.6–94.6 |
| N-5 | ¼" | 24 | 750–32 | 103.4–105.4 | 91.4–93.4 |
| K-5 | ¼"* | 44 | 750–40 | 119.0–120.5 | 100.2–103.0 |
| K-5 | ¼"* | 24 | 750–40 | 110.0–112.0 | 93.5–95.5 |
| K-5 | ¼"** | 44 | 750–32 | 110.0–112.0 | 91.7–94.2 |
| K-5 | ¼"** | 26 | 750–32 | 102.0–104.0 | 87.2–89.7 |
| K-5 | ¼"* | 44 | 350–40 | 112.7–115.0 | 99.7–102.0 |
| K-5 | ¼"** | 26 | 350–40 | 110.7–112.7 | 95.0–97.0 |
| K-5 | ¼"** | 44 | 350–32 | 108.7–110.7 | 92.5–94.5 |

TABLE I-continued

CARBON-GRAPHITE ELECTRODES AT HIGH AND LOW AIR FLOW

| Type of Torch | Type of Electrode | Air Flow (SCFH) | Power AMPS Volts | Noise Level, dba Outside Helmet | Users Ear |
|---|---|---|---|---|---|
| K-5 | ⅜"* | 26 | 350–32 | 107.5–109.5 | 89.2–91.2 |

NOTES:
Torches - Arcair K-5 Hand held Torch, Arcair N-5 Automatic with 17 Hole Nozzle.
Power Supply:
Arcair LSC Model 1000 used with N-5
Miller 1500 used with K-5 at 750 AMPS
Miller 600 used with K-5 at 350 AMPS
Distance From Air Orifice to ARC: 3" with N-5 C" with K-5
Sound Meters: General radio 1933 S.L.M. used for overall noise level readings. Reading made 20 inches from arc outside of Helmet. Scott 450 with extension microphone used for noise readings inside helmet. Extension microphone placed at operator's ear - approximately 20 inches from arc.
*Conventional Direct Current Copper Coated Electrode
**Conventional Copper coated electrode containing proprietary additives for noise reduction From the foregoing Table I, it is readily apparent that there is a significant reduction in operating noise level when the operator is wearing a helmet with noise attenuating ear protectors such as shown in FIGS. 1–3 of the drawing. Even when the process air pressure is reduced to reduce the operating noise level, the improved helmet gives further beneficial reductions in the noise presented to a welder's ear.

Figure 4:
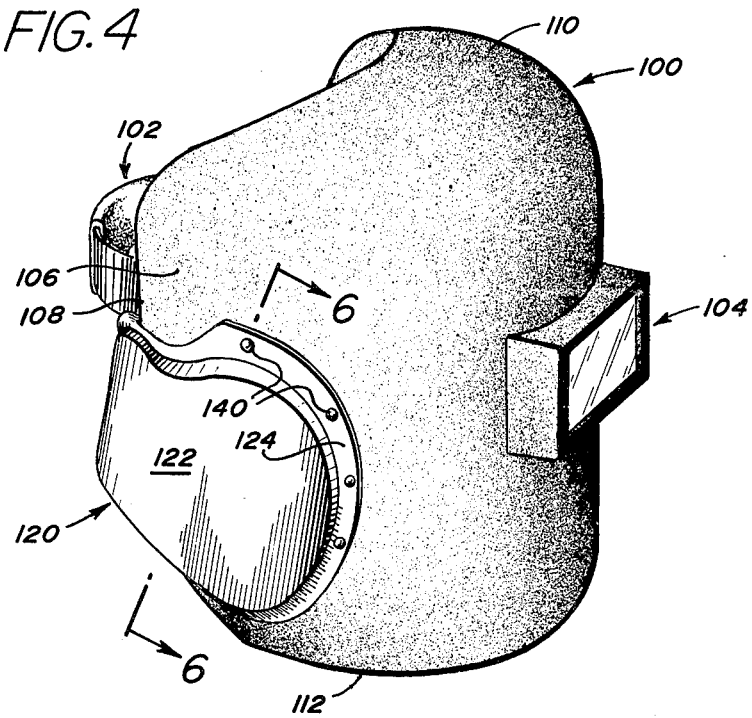
FIG. 4 is a perspective view of a conventional welding helmet having an ear protection device according to the present invention fitted thereon.

FIG. 4 shows a conventional welder's helmet 100 including a head supporting harness 102 similar to the head supporting harness 30 of the helmet of FIG. 1, and a viewing port shown generally as 104 closed by a light filtering window similar to that of the helmet of FIG. 1.

Figure 5:
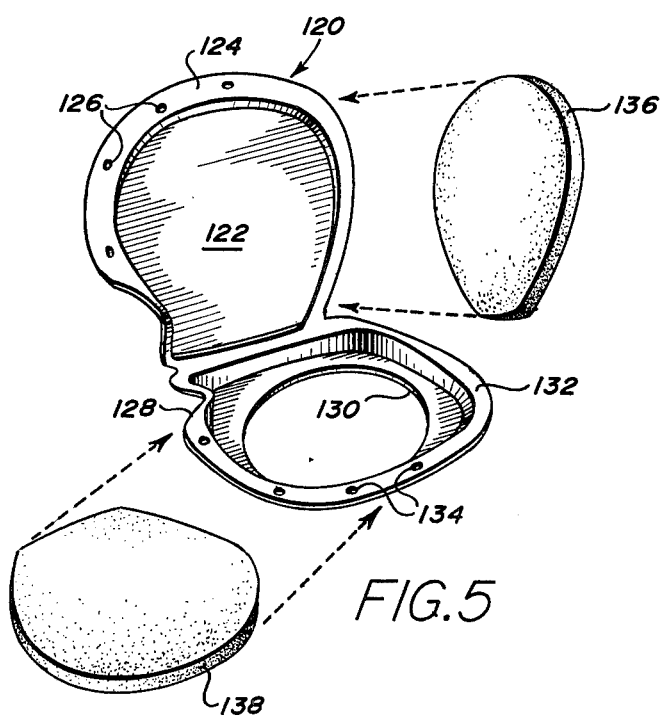
FIG. 5 is an exploded view of the ear protection device of FIG. 4 shown removed from the helmet.
Figure 6:
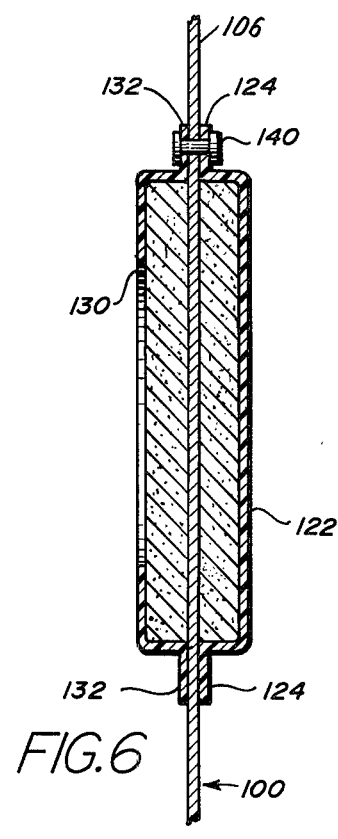
FIG. 6 is a fragmentary section taken along the line 6—6 of FIG. 4.

The helmet 100 has rearwardly extending sides, one of which 106 is shown in the drawing. The side 106 terminates in a generally vertically extending edge 108 which extends from the forehead protection portion 110 to the chin and neck protection portion 112 of helmet 100. Fitted on either side of helmet 100 is an ear protection device shown generally as 120. Referring to FIG. 5, the ear protection device 120 has a clam-like support structure including a first half 122 in the shape of a dish with a raised lip 124 having therein a plurality of apertures 126. Hingedly connected to the first half 122 of ear protector 120 is a second support half 128 being a mirror image of section 122 of ear protector 120. A large annular aperture 130 opens the bottom of the dish-like portion of 128 to the atmosphere. Second half 128 includes a flat annular lip 132 and apertures 134 each of which are complementary to apertures 126 of section 122. Disposed within the dish-like portions 122 and 128 of ear protector 120 are a pair of foam pads 136, 138 of an acoustical absorbing material. This material can be the same foamed polymeric material used in the device of FIGS. 1–3. The ear protector 120 is affixed to the helmet 100 by closing the halves 122, 128 (clam) to grip the respective sides of the helmet 100 such as shown in FIG. 4. The ear protector 120 is fastened to the helmet 100 by passing a plurality of fasteners, e.g. rivets 140 through the mating apertures 126, 134 and through the respective sidewall of the helmet 100. Of course the ear protector 120 can be fastened to the helmet by a suitable adhesive between the lip 124, 132 and the sidewall of the helmet. The ear protector 120 is positioned so that the half of the protector 120 having the large aperture 130 is on the inside surface of the helmet so that the acoustical sound absorbing material is positioned adjacent the welder's ear in the manner of the device shown in FIG. 3. This apparatus of FIGS. 4–6 is a device that can be readily attached to existing welding helmets to provide the same type of noise reduction experienced with the device of FIGS. 1–3. The point of fact, a device was constructed according to that shown in FIGS. 4–6 and the tests as set forth in Table II below confirmed almost identical noise level readings to those shown in Table I.

Figure 7:
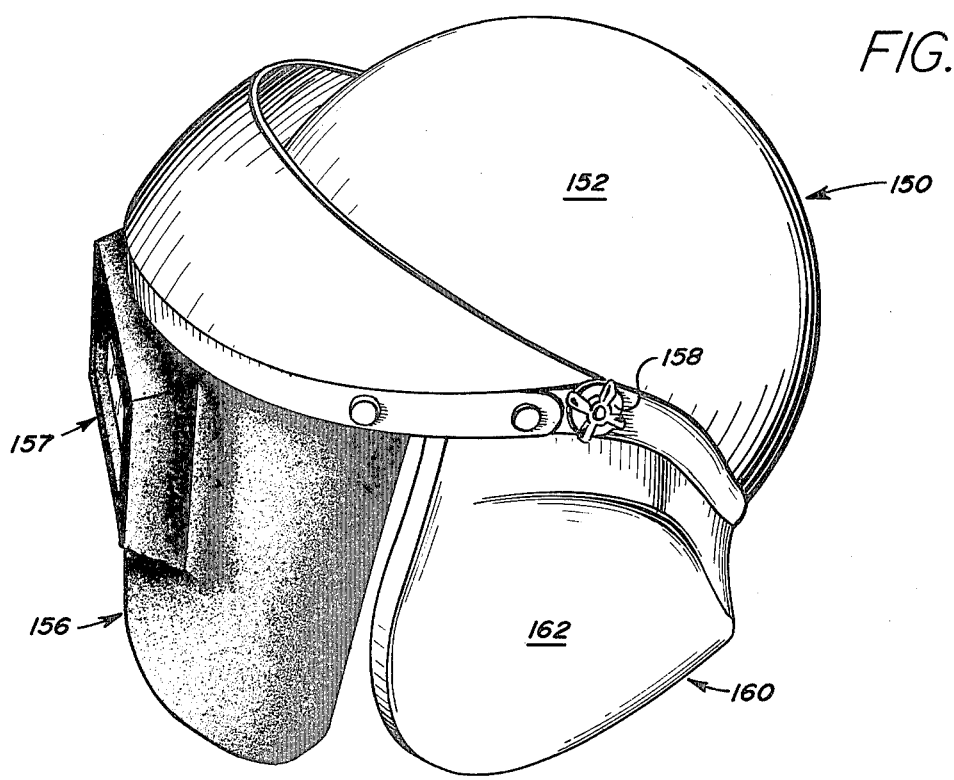
FIG. 7 is a partial side perspective view of a conventional "hard hat" with noise attenuators according to the present invention.
Figure 8:
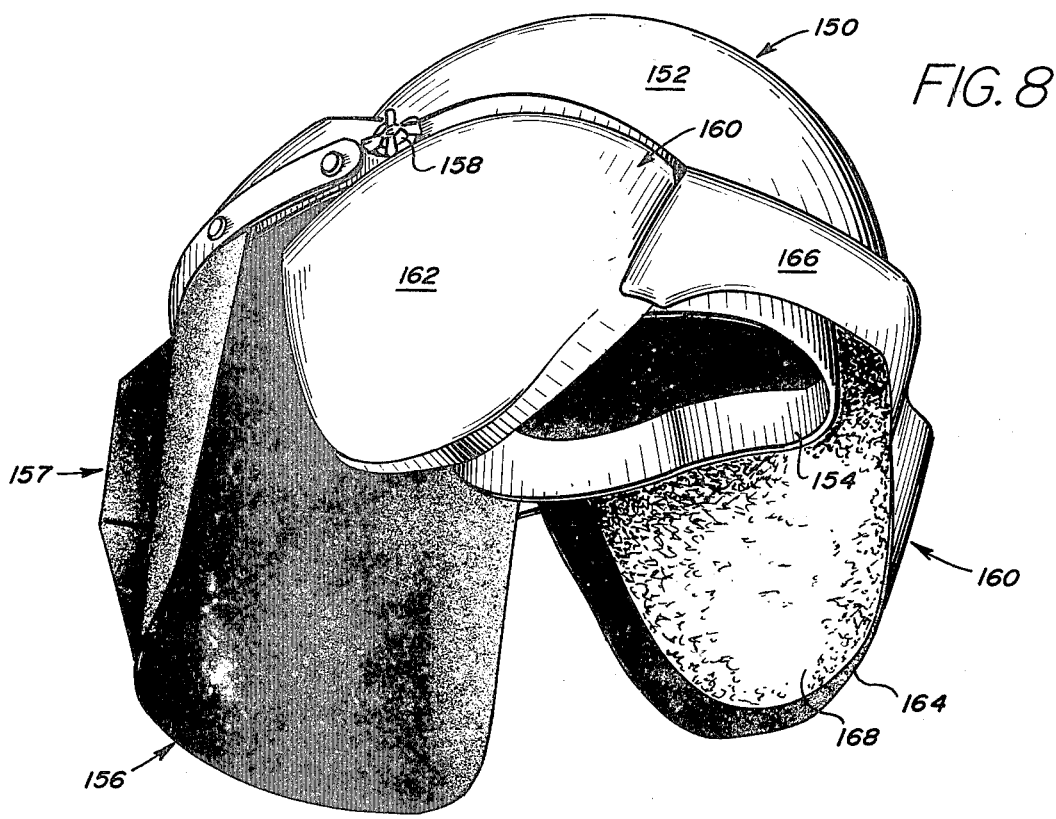
FIG. 8 is a partial bottom perspective view of the device of FIG. 7.

FIGS. 7 and 8 show an apparatus according to the invention as it can be applied to an ordinary safety helmet (hard hat). The hard hat 150 is of the conventional type having an outer shell 152 and inner head harness 154 (FIG. 8) support as is well-known in the art. A face shield 156 is hingedly fixed to hard hat 150 as by adjustable pivot members, one of which is shown as 158. Pivot member 158 is similar to pivot members 36 and 38 of the device of FIGS. 1–3 and permits face shield 156 containing tinted safety window 157 to be moved into position in front of the wearer's face as welding takes place or away from the wearer's face to facilitate material handling and set-up before or after welding.

Ear protector device 160 consisting of two ear pieces 162 and 164 joined by a spacer or support 166 is fastened to hard hat 150 by any convenient means, e.g. adhesive, ear protector 160 supports an inner lining of acoustical foam material adjacent to but not in contact with the wearer's ear thus achieving the same noise attenuating characteristics found with the devices of FIGS. 1 through 6.

Table II sets forth the results of a series of tests run with a device such as shown in FIGS. 7 and 8. The test data shown in Table II show the device of FIGS. 7 and 8 to be effective in reducing noise at the wearer's ear.

TABLE II

| Type of Torch | Type of Electrode | Air Flow (mm) | Power Amps | Volts | Noise Level dbA Outside Helmet | User's Ears |
|---|---|---|---|---|---|---|
| N-5 | ⅜"* | 200 | 740 | 40 | 120–125 | 106–108 |
| N-5 | ⅜"** | 150 | 740 | 40 | 104–107 | 86–89 |
| N-5 | ⅜"* | 150 | 750 | 40 | 117–119 | 105–107 |
| N-5 | ⅜"** | 150 | 750 | 32 | 107–109 | 45–97 |
| N-5 | ⅜"* | 200 | 740 | 40 | 120–125 | 104–108 |

TABLE II-continued

| Type of Torch | Type of Electrode | Air Flow (mm) | Power Amps | Volts | Noise Level dbA Outside Helmet | User's Ears |
|---|---|---|---|---|---|---|
| N-5 | ½"** | 150 | 750 | 32 | 108–110 | 90–91 |

NOTES:
Torch: Arcair N-5 Automatic Torch with 17 hole nozzle
Power Supply: Arcair LSC Model 1000
Distance from air orifice to arc: 6"
Sound equipment: Anechoic chamber of 1" thick styrofoam lined with 3" layer of commercial fiberglass insulation; General Radio 1933 S.L.M. used for overall noise level readings. Reading made 20" from arc outside helmet. Scott 452 with extension microphone used for noise readings inside helmet. Extension microphone placed at operator's ear - approximately 20" from arc.
Air flow: Muffled air measured by a Brooks rotometer
*Conventional direct current copper coated electrode
**Conventional copper coated electrode containing proprietary additives for noise reduction In order to effect even more sound reduction, it would be within the scope of the present invention to line the entire interior surface, excluding the viewing port, of the welding helmet with the sound absorbing material. Tests with this type of helmet confirmed slightly better sound attenuating characteristics with the full helmet lining.

It is within the scope of the present invention to mold the ear protecting housing 56 of the apparatus of FIGS. 1-3 as an integral unit with the helmet allowing for insertion of the sound absorbing material after the molding operation.

It should be borne in mind that the object of the present invention is to provide a welding helmet wherein the noise level surrounding the user is not transmitted in total to his ears. This is to be done while eliminating the need for the "ear-muff" type sound blocking devices. It has been industry experience that "ear-muff" type sound blocking devices are uncomfortable especially when an operator is working in high temperature environments because of the attendant perspiration and irritation of the skin under the ear-muff. The ear-muff device also represents another piece of equipment that must be purchased and maintained, and use must be enforced to prevent hearing damage. With the device of the instant invention, ear protection comes along with face and eye protection which every welder must use.

The apparatus of the present invention does not interfere with atmospheric circulation inside the welding helmet and does not increase the welder discomfort since there is no device exerting pressure on the ear of the user.

In summary, it should be noted that by using current molding techniques, the single unit welding helmet can be made light in weight and will provide in the same unit ear protection whether or not the user wishes to have the same. Foreclosing, the choice protects the user by reducing the ambient noise level 10 to 15 dbA under the welding helmet.

It is also within the scope of the present invention to include back and bottom flaps that can be caused to open or close as the helmet is raised or lowered about the pivot points to further protect the welder's ears form noise without contacting the ears or the head around the ears of the welder/user.

Devices, according to the present invention, can be made to be accessories which depend from conventional "hard-hats" to effect noise protection in working environments.

The sound absorbing materials can be readily replaced either because of wear, cleaning, or to use improved materials as they are developed.

It is also possible to further minimize noise level by sealing the viewing port area of the face shield with appropriate gaskets so that noise does not filter in through gaps at the glass to viewing port interface. The entire helmet and sound absorbing materials are easily accessible for cleaning so that the sound absorbing qualities will not be destroyed by the material becoming filled with foreign particulate matter, or vaporized or liquid materials.

Having thus described our invention, what we desire to be secured by Letters Patent of the United States is set forth in the appended claims.

We claim:

1. In a welder's helmet of the type having a front section containing a light filtering glass window and oppositely disposed rearwardly extending sides supported by a head harness for positioning the helmet to protect the face and sides of a welder's head when the helmet is worn during a welding operation, the improvement comprising:
   a forward extending recess in each of said sides, said recess sized to be larger than the area covering a welder's ears;
   ear protection means including an acoustical absorbing medium covering said recesses and extending rearwardly therefrom, said means and acoustical medium being disposed in said recesses so that when said helmet is being worn, neither said means nor said acoustical absorbing medium touches the ears of the user/welder.

2. A helmet according to claim 1 wherein said acoustical absorbing medium is a synthetic foam material.

3. A helmet according to claim 1 wherein said ear protection means includes a support structure having the shape of an annulus wherein the peripheral shape of the annulus is complementary to said recess and having disposed therein acoustical foam.

4. A helmet according to claim 3 wherein the surfaces of said support positioned outwardly of said helmet are of a sound reflecting material.

5. Ear protection device for placing on a welding helmet of the type having a front section containing a light filtering glass window and oppositely disposed rearwardly extending sides supported by a head harness for positioning the helmet to protect the face and sides of welder's head when the helmet is worn during a welding or gouging operation comprising in combination:
   an acoustical structure having a first half and a second half, said second half having a large generally circular aperture;
   an acoustical sound absorbing medium disposed in each of said halves of said support structure; and
   means to position and fix one of said support structures on each of said rearwardly extending portions of said helmet, whereby said support half having the aperture is positioned adjacent to but spaced apart from the ear of a welder when said helmet is in use.

6. An ear protector according to claim 5 wherein said acoustical support structure is generally clam shaped and said first and second halves are hingedly connected.

7. An ear protector according to claim 5 wherein said acoustical sound absorbing medium is a synthetic foam.

8. An ear protector according to claim 5 wherein said means to position and fix said support structure includes a generally flat annular lip on each of said halves having a plurality of apertures therein to receive mechanical fasteners extending through one of said lips through said helmet and through said other lip of said support structure.

9. An ear protector according to claim 8 wherein said fasteners are rivets.

10. Ear protection device adapted to be fitted to a head protecting device of the hard hat type, consisting of an outer shell and inner harness to protect the upper head of a wearer, comprising in combination:

a first ear piece and a second ear piece each having an outer surface and an inner surface lined with an acoustical sound absorbing medium; and means to position said first and second ear pieces on the hard hat so that said sound absorbing medium is spaced adjacent the wearers ear without physically touching the wearer's ear said means includes a support fixed to each ear piece and adapted to fasten said ear pieces to said hard hat by suitable fastening means.

11. An ear protection device according to claim 10 wherein said acoustical sound absorbing medium is a synthetic foam.

* * * * *